(12) United States Patent
Den Boef et al.

(10) Patent No.: US 8,830,455 B2
(45) Date of Patent: Sep. 9, 2014

(54) INSPECTION METHOD AND APPARATUS

(75) Inventors: Arie Jeffrey Den Boef, Waalre (NL);
Vadim Yevgenyevich Banine, Eendracht (NL); Sander Frederik Wuister, Eindhoven (NL); Luigi Scaccabarozzi, Valkenswaard (NL)

(73) Assignee: ASML Netherlands B.V., Veldhoven (NL)

( * ) Notice: Subject to any disclaimer, the term of this patent is extended or adjusted under 35 U.S.C. 154(b) by 141 days.

(21) Appl. No.: 12/805,808

(22) Filed: Aug. 19, 2010

(65) Prior Publication Data

US 2011/0043795 A1 Feb. 24, 2011

Related U.S. Application Data

(60) Provisional application No. 61/235,794, filed on Aug. 21, 2009.

(51) Int. Cl.
*G01N 21/00* (2006.01)

(52) U.S. Cl.
USPC .................................. 356/237.3; 356/237.5

(58) Field of Classification Search
USPC ........... 356/237.1–237.5, 239.5, 239.7, 239.8
See application file for complete search history.

(56) References Cited

U.S. PATENT DOCUMENTS

| 4,297,032 | A | * | 10/1981 | Temple | 356/366 |
| 4,469,442 | A | | 9/1984 | Reich | |
| 4,731,155 | A | | 3/1988 | Napoli et al. | |
| 4,952,058 | A | * | 8/1990 | Noguchi et al. | 356/237.5 |
| 5,208,648 | A | * | 5/1993 | Batchelder et al. | 356/237.1 |
| 5,410,400 | A | * | 4/1995 | Shishido et al. | 356/237.4 |
| 5,772,905 | A | | 6/1998 | Chou | |
| 5,777,729 | A | | 7/1998 | Aiyer et al. | |
| 6,084,664 | A | * | 7/2000 | Matsumoto et al. | 356/237.4 |
| 6,334,960 | B1 | | 1/2002 | Willson et al. | |
| 6,774,989 | B1 | * | 8/2004 | Rangarajan et al. | 356/237.2 |
| 7,019,835 | B2 | * | 3/2006 | McMackin et al. | 356/394 |
| 7,109,458 | B2 | * | 9/2006 | Fairley et al. | 250/201.3 |
| 7,130,037 | B1 | * | 10/2006 | Lange | 356/237.2 |
| 7,169,514 | B2 | | 1/2007 | Lee | |
| 7,710,572 | B2 | | 5/2010 | Mos et al. | |

(Continued)

FOREIGN PATENT DOCUMENTS

| CN | 1898603 | 1/2007 |
| CN | 101236359 | 8/2008 |

(Continued)

OTHER PUBLICATIONS

Korean Office Action dated Aug. 31, 2011 in corresponding Korean Patent Application No. 10-2010-0080973.

(Continued)

*Primary Examiner* — Hoa Pham
(74) *Attorney, Agent, or Firm* — Pillsbury Winthrop Shaw Pittman LLP

(57) ABSTRACT

In an aspect, an inspection method for detecting the presence or absence of a defect on an object, the object comprising a recess having a physical depth, is disclosed. The method includes directing radiation at the object, the radiation having a wavelength that is substantially equal to twice an optical depth of the recess, detecting radiation that is re-directed by the object or a defect on the object, and determining the presence or absence of a defect from the re-directed radiation.

19 Claims, 6 Drawing Sheets

(56) References Cited

U.S. PATENT DOCUMENTS

| | | | |
|---|---|---|---|
| 7,858,911 B2* | 12/2010 | Fairley et al. | 250/201.3 |
| 7,911,600 B2* | 3/2011 | Terasawa et al. | 356/237.5 |
| 2002/0015146 A1 | 2/2002 | Meeks et al. | |
| 2002/0017620 A1 | 2/2002 | Oomori et al. | |
| 2004/0032593 A1 | 2/2004 | Venugopal | |
| 2004/0124566 A1 | 7/2004 | Sreenivasan et al. | |
| 2005/0147894 A1 | 7/2005 | Lee | |
| 2005/0274693 A1 | 12/2005 | Heidari et al. | |
| 2006/0268256 A1 | 11/2006 | Kolesnychenko et al. | |
| 2007/0018360 A1 | 1/2007 | Kolesnychenko et al. | |
| 2007/0035726 A1* | 2/2007 | Takahashi et al. | 356/237.1 |
| 2007/0076195 A1 | 4/2007 | Yamaguchi et al. | |
| 2008/0128644 A1 | 6/2008 | Mos et al. | |
| 2009/0002695 A1 | 1/2009 | Saito et al. | |
| 2009/0091752 A1 | 4/2009 | Terasawa et al. | |
| 2009/0113704 A1* | 5/2009 | Toyoda | 29/850 |
| 2010/0315643 A1* | 12/2010 | Kashiwagi et al. | 356/433 |
| 2011/0129930 A1* | 6/2011 | Wuister | 436/35 |

FOREIGN PATENT DOCUMENTS

| | | |
|---|---|---|
| JP | 2006-332678 | 12/2006 |
| JP | 2008-116272 | 5/2008 |
| JP | 2009-092407 | 4/2009 |
| KR | 86-0002073 | 11/1986 |
| WO | 02/067055 A2 | 8/2002 |

OTHER PUBLICATIONS

J. Haisma et al., "Mold-assisted nanolithography: A process for reliable patter replication," J. Vac. Sci. Technol. B 14(6), Nov./Dec. 1996, pp. 4124-4128.

Japanese Office Action mailed Mar. 2, 2012 in corresponding Japanese Patent Application No. 2010-181487.

Chinese Office Action dated Jan. 4, 2012 in corresponding Chinese Patent Application No. 201010262277.3.

Chinese Office Action dated Sep. 27, 2012 in corresponding Chinese Patent Application No. 201010262277.3.

* cited by examiner

INSPECTION METHOD AND APPARATUS

This application claims priority and benefit under 35 U.S.C. §119(e) to U.S. Provisional Patent Application No. 61/235,794, entitled "Inspection Method and Apparatus", filed on Aug. 21, 2009, The content of the foregoing application is incorporated herein in its entirety by reference.

FIELD

The present invention relates to an inspection method and apparatus. The inspection method and apparatus may be used, for example (and not exclusively) to inspect an imprint lithography template.

BACKGROUND

In lithography, there is an ongoing desire to reduce the size of features in a lithographic pattern in order to increase the density of features on a given substrate area. In photolithography, the push for smaller features has resulted in the development of technologies such as immersion lithography and extreme ultraviolet (EUV) lithography, which are however rather costly.

A potentially less costly road to smaller features that has gained increasing interest is so-called imprint lithography, which generally involves the use of a "stamp" (often referred to as an imprint template or an imprint lithography template) to transfer a pattern onto a substrate. An advantage of imprint lithography is that the resolution of the features is not limited by, for example, the emission wavelength of a radiation source or the numerical aperture of a projection system. Instead, the resolution is mainly limited to the pattern density on the imprint template.

Imprint lithography involves the patterning of an imprintable medium on a surface of a substrate to be patterned. The patterning may involve bringing together a patterned surface of an imprint template and a layer of imprintable medium (e.g., moving the imprint template toward the imprintable medium, or moving the imprintable medium toward the imprint template, or both) such that the imprintable medium flows into recesses in the patterned surface and is pushed aside by protrusions on the patterned surface. The recesses define pattern features of the patterned surface of the imprint template. Typically, the imprintable medium is flowable when the patterned surface and the imprintable medium are brought together. Following patterning of the imprintable medium, the imprintable medium is suitably brought into a non-flowable or frozen state (i.e. a fixed state) and the patterned surface of the imprint template and the patterned imprintable medium are separated. The substrate and patterned imprintable medium are then typically processed further in order to pattern or further pattern the substrate. The imprintable medium is typically provided in the form of droplets on the surface of a substrate to be patterned, but may alternatively be provided using spin coating or the like.

SUMMARY

During use of an imprint template, the imprint template may accumulate a defect. For example, a defect may be one or more particles of imprintable medium that have become deposited on the imprint template during an imprint process. If such a defect is not removed, in a subsequent imprint of the imprint template the defect may be physically transferred onto or into the imprintable medium, or the defect may itself provide a corresponding pattern in the imprintable medium. In either example, the pattern that has imprinted into the imprintable medium may be defective.

In order to obviate or mitigate the problem of a defect accumulating on the imprint template, it is desirable to be able to inspect an imprint template in order to detect the presence (or absence) of such a defect. A defect may be removed once detected. Such inspection could, for example, be undertaken using a scanning electron microscope. However, such an inspection method can be slow, and may therefore be undesirable. Another inspection method involves detecting the presence of a defect by detecting radiation scattered by the defect. However, in this method radiation is also scattered by the pattern features of the imprint template itself (e.g. recesses of the imprint template), and this can make it difficult or impossible to be able to accurately and consistently detect scattering from the defect, and thus the presence of the defect. If the pattern features of the imprint template are periodic, scattering from the periodic pattern features can be suppressed to some extent with a spatial filter. However, spatial filtering does not work for non-periodic pattern features, and an imprint template often comprises non-periodic pattern features. Other approaches are also possible which take into account the non-periodic nature of the pattern features, but these approaches require prior knowledge of the layout (i.e. design) of the non-periodic pattern features. It is desirable to avoid the requirement of such prior knowledge.

It is desirable, for example, to provide an inspection method and apparatus that obviates or mitigates at least one problem of the art, whether identified herein or elsewhere, or which provides an alternative to an existing inspection method and apparatus.

According to an aspect, there is provided an inspection method for detecting the presence or absence of a defect on an object, the object comprising a recess having a physical depth, the method comprising: directing radiation at the object, the radiation having a wavelength that is substantially equal to twice an optical depth of the recess (which is equal to the physical depth of the recess multiplied by the refractive index of the medium or vacuum in the recess); detecting radiation that is re-directed by the object or a defect on the object; and determining the presence or absence of a defect from the re-directed radiation.

According to an aspect, there is provided an inspection method for detecting the presence or absence of a defect on an object, the object comprising a recess having a physical depth, the method comprising: providing a liquid that is in contact with the object; directing radiation through the liquid and at the object, the liquid having a refractive index which substantially matches that of the object for a wavelength of the radiation; detecting radiation re-directed by the object or a defect on the object; and determining the presence or absence of a defect from the re-directed radiation. The radiation may have a wavelength in the liquid that is substantially equal to twice an optical depth of the recess (which is equal to the physical depth of the recess multiplied by the refractive index of the medium or vacuum in the recess).

In the aspects above, the object may be an imprint template, or a mask suitable for use in EUV lithography.

In the aspects above, the optical (or physical) depth of the recess may be of the order of nanometers, in the range of 0 nm to 100 nm, or in the range of 40 nm to 70 nm. The physical depth of the recess may be 4 nm or more, to allow for etch selectivity.

In the aspects above, the radiation may have a wavelength of the order of nanometers, in the range of 0 nm to 200 nm, or in the range of 80 nm to 140 nm.

In the aspects above, the radiation may be substantially monochromatic, or include a narrow range of wavelengths.

In the aspects above, the re-directed radiation may comprise scattered radiation.

In the aspects above, the presence or absence of the defect may be detected from an intensity distribution, or a change in an intensity distribution, of the re-directed radiation.

In the aspects above, the presence or absence of the defect may be detected using dark field imaging.

In the aspects above, the object may comprise a plurality of recesses. The plurality of recesses may be arranged in a non-periodic manner.

In the aspects above, the object may comprise fused silica or quartz.

According to an aspect, there is provided an inspection apparatus to detect the presence or absence of a defect on an object, the object comprising a recess having a physical depth, the apparatus comprising: a radiation outlet configured to direct radiation at the object, the radiation outlet configured to direct radiation having a wavelength that is substantially equal to twice an optical depth of the recess (which is equal to the physical depth of the recess multiplied by the refractive index of the medium or vacuum in the recess); a detector configured to detect the radiation that is re-directed by the object or a defect on the object; and a detection arrangement configured to determine the presence or absence of a defect using the re-directed radiation.

According to an aspect, there is provided an inspection apparatus to detect the presence or absence of a defect on an object, the object comprising a recess having a physical depth, the apparatus comprising: a liquid dispenser configured to provide a liquid on, and in contact with, the object; a radiation outlet configured to, in use, direct radiation through the liquid and at the object, the liquid having a refractive index which substantially matches that of the object for a wavelength of the radiation; a detector configured to detect the radiation that is re-directed by the object or a defect on the object; and a detection arrangement configured to determine the presence or absence of a defect using the re-directed radiation.

According to an aspect, there is provided an object comprising a recess having an optical depth (which is equal to the physical depth of the recess multiplied by the refractive index of the medium or vacuum in the recess) substantially equal to half the wavelength of radiation that is, in use, directed at the object to detect the presence or absence of a defect on the object.

The inspection apparatus and object aspects may have or comprise, where appropriate, any one or more features described above.

According to any aspect, the object may be an imprint template, or a mask suitable for use in EUV lithography.

BRIEF DESCRIPTION OF THE DRAWINGS

Specific embodiments of the invention will be described with reference to the accompanying Figures, in which.

DETAILED DESCRIPTION

Figure 1A:
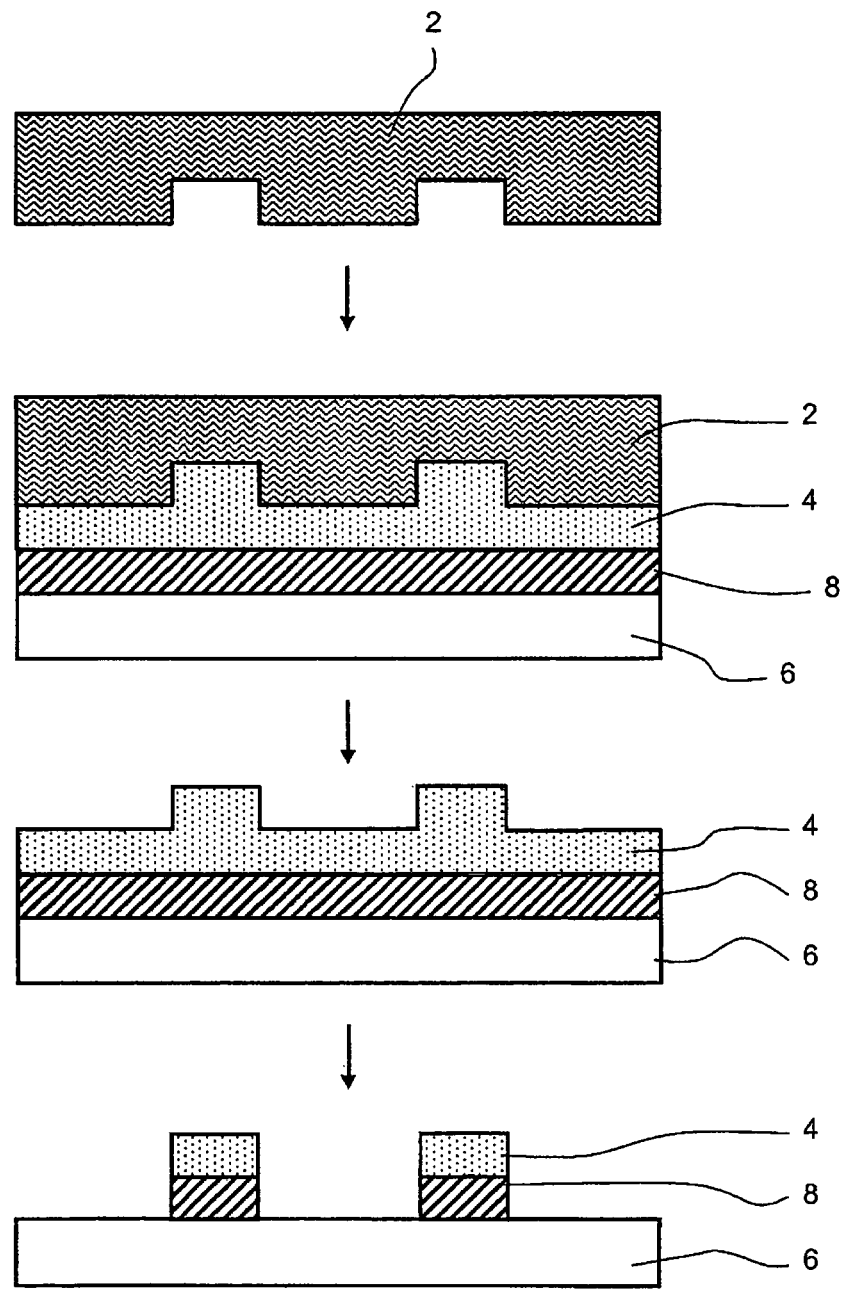
FIGS. 1a and 1b schematically depict examples of, respectively, hot imprint, and UV imprint lithography.
Figure 1B:
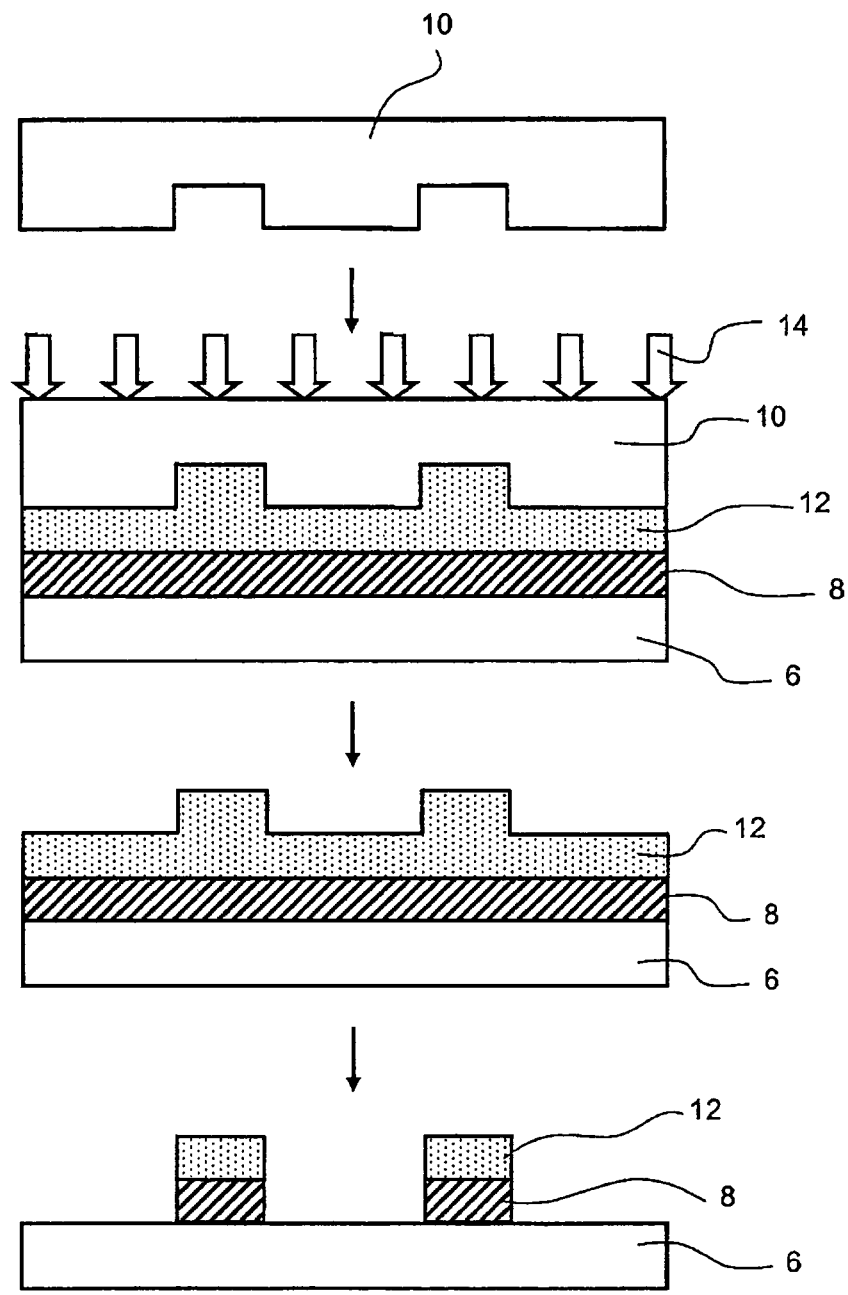

Examples of two approaches to imprint lithography are schematically depicted in FIGS. 1a and 1b.

FIG. 1a shows an example of so-called hot imprint lithography (or hot embossing). In a typical hot imprint process, an imprint template 2 is imprinted into a thermosetting or a thermoplastic imprintable medium 4, which has been provided on the surface of a substrate 6. The imprintable medium 4 may be, for example, resin. The imprintable medium 4 may for instance be spin coated and baked onto the substrate surface or, as in the example illustrated, onto a planarization and transfer layer 8 of the substrate 6. When a thermosetting polymer resin 4 is used, the resin 4 is heated to a temperature such that, upon contact with the imprint template 2, the resin 4 is sufficiently flowable to flow into the pattern features defined on the imprint template 2. The temperature of the resin 4 is then increased to thermally cure (crosslink) the resin 4 so that it solidifies and irreversibly adopts the desired pattern. The imprint template 2 may then be removed and the patterned resin 4 cooled. In hot imprint lithography employing a layer of thermoplastic polymer resin 4, the thermoplastic resin is heated so that it is in a freely flowable state immediately prior to imprinting with the imprint template. It may be necessary to heat thermoplastic resin to a temperature considerably above the glass transition temperature of the resin. The imprint template is contact with the flowable resin and then the resin is cooled to below its glass transition temperature with the imprint template in place to harden the pattern. Thereafter, the template is removed. The pattern will consist of the features in relief from a residual layer of the resin which may then be removed by an appropriate etch process to leave only the pattern features. Examples of thermoplastic polymer resins used in hot imprint lithography processes are poly (methyl methacrylate), polystyrene, poly (benzyl methacrylate) or poly (cyclohexyl methacrylate). For more information on hot imprint, see e.g. U.S. Pat. Nos. 4,731,155 and 5,772,905.

FIG. 1b shows an example of UV imprint lithography, which involves the use of a transparent or translucent imprint template 10 which is transmissive to UV radiation and a UV-curable liquid as imprintable medium 12 (the term "UV" is used here for convenience but should be interpreted as including any suitable actinic radiation for curing the imprintable medium). A UV curable liquid is often less viscous than the thermosetting and thermoplastic resins used in hot imprint lithography and consequently may move much faster to fill imprint template pattern features. A quartz template 10 is applied to a UV-curable imprintable medium 12 in a similar manner to the process of FIG. 1a. However, instead of using heat or temperature cycling as in hot imprint lithography, the pattern is frozen by curing the imprintable medium 12 with UV radiation 14 that is applied through the quartz imprint template 10 onto the imprintable medium 12. After removal of the imprint template 10, the imprintable medium 12 is etched (and/or undergoes other further processing) to, for example provide pattern features in the substrate 6. A particular manner of patterning a substrate through UV imprint lithography is so-called step and flash imprint lithography (SFIL), which may be used to pattern a substrate in small steps in a similar manner to optical steppers conventionally used in IC manufacture. For more information on UV imprint, see e.g. U.S. Patent Application Publication No. 2004-0124566, U.S. Pat. No. 6,334,960, PCT Patent Application Publication No. WO 02/067055, and the article by J. Haisma entitled "Mold-assisted nanolithography: A process for reliable pattern replication", J. Vac. Sci. Technol. B14(6), November/December 1996.

Combinations of the above imprint techniques are also possible. See, e.g., U.S. Patent Application Publication No. 2005-0274693, which mentions a combination of heating and UV curing an imprintable medium.

During use, an imprint template may accumulate one or more defects, such as particles of imprintable medium or other contamination. If not detected and removed, during subsequent imprints of the imprint template the defect may be physically transferred to the imprintable medium, or the defect may provide a pattern feature in the imprintable medium. In either example, the imprinted pattern may be defective. It is therefore desirable to be able to inspect the imprint template in order to detect the presence of a defect, and subsequently remove that defect.

Figure 2:
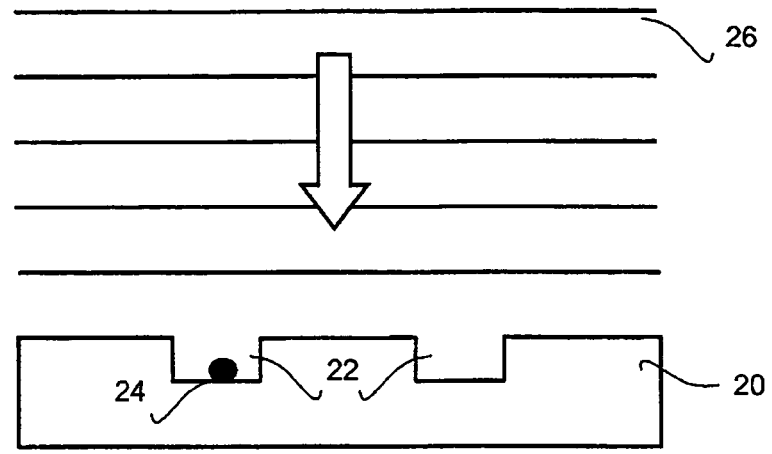
FIG. 2 schematically depicts principles associated with an inspection method.

An inspection method for detecting the presence of a defect on an imprint template is shown in FIG. 2. FIG. 2 schematically depicts an imprint template 20 (for example, the imprint template shown in and described with reference to FIGS. 1a and/or 1b). Recesses 22 in the imprint template 20 provide pattern features which may be used to provide a pattern in imprintable medium. Located in a recess 22 of the imprint template 20 is a defect 24 in the form of a particle.

The inspection method comprises directing radiation 26 at the imprint template 20. The radiation 26 may be directed at a specific local area or a large area (e.g. a majority or all of the area) of the imprint template 20 at any one time. Alternatively or additionally, the radiation 26 (or a source of the radiation) may be moved relative to the imprint template 20 (and/or the imprint template 20 may be moved relative to the radiation 26) to inspect a part of or the entire imprint template 20.

Figure 3:
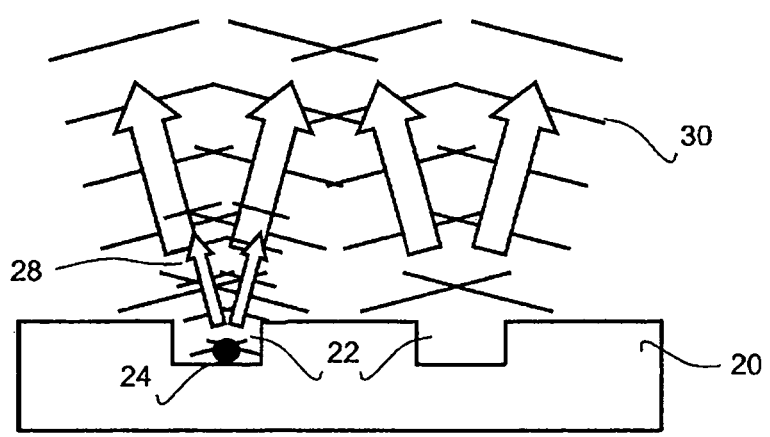
FIG. 3 schematically depicts further principles associated with the inspection method shown in and described with reference to FIG. 2.

FIG. 3 shows that radiation is re-directed (i.e. scattered, in this embodiment) by the imprint template 20 and the defect 24. Specifically, a small portion of radiation 28 is scattered by the defect 24. A much larger portion of radiation 30 is scattered by pattern features (e.g. recesses 22 and protrusions formed by the provision of those recesses 22) of the imprint template 20. The scattering of the much larger portion of radiation 30 makes it difficult or impossible to be able to accurately and consistently detect the smaller portion of radiation 28 scattered by the defect 24. Because this smaller portion of radiation 28 cannot be detected well or at all, the presence of the defect 24 can also not be detected well or at all.

In order to be able to detect the defect 24, it is desirable to be able to reduce the (larger portion of) radiation scattered by the pattern features of the imprint template 20. Such reduction may be achieved according to embodiments of the present invention.

According to an embodiment, there is provided an inspection method for detecting the presence of a defect on an object. The object may be, for example, an imprint template or a mask suitable for use in EUV lithography (for example, a reflective mask comprising one or more recesses). The object comprises at least one recess which has a physical depth (or an optical depth, which is equal to the physical depth of the recess multiplied by the refractive index of the medium or vacuum in the recess). The method comprises directing radiation at the object. The radiation has a wavelength that is substantially equal to twice the optical depth of the recess. Radiation that is re-directed by the object (e.g. scattered or reflected) is then detected (for example, by a detector or a detection arrangement). The presence of a defect is detected from the re-directed radiation, for example from an intensity distribution, or a change in an intensity distribution, of the re-directed radiation.

Since the wavelength of the radiation is substantially equal to twice the optical depth of the recess, the scattering of radiation from pattern features of the object (e.g. recesses or the like) will be significantly reduced. This is because the phase difference between radiation re-directed from a bottom of the recess and a top of the recess will be equal to $2\pi$. In this case, the near-field of the scattered radiation will ideally be continuous which will result in only a specular reflection of the radiation that can be effectively suppressed with a 0-order stop. Detection of the defect should therefore be easier to achieve. This effect may still be achieved if the wavelength of radiation is a few nanometers (i.e. 0-5 nm or 0-3 nm) longer or shorter than the optical or physical depth of the recess (this being substantially equal to the optical depth of the recess).

According to a further embodiment, there is provided an inspection method for detecting the presence of a defect on an object. The object may be, for example, an imprint template or a mask suitable for use in EUV lithography (for example, a reflective mask comprising one or more recesses). The object comprises at least one recess which has a physical depth (or an optical depth, which is equal to the physical depth of the recess multiplied by the refractive index of the medium or vacuum in the recess). The method comprises providing a liquid that is in contact with the object. Radiation is then directed through the liquid and at the object. The liquid has a refractive index which substantially matches that of the object for a wavelength of the radiation (or a range of wavelengths). In one example, a difference between the refractive index of the liquid and that of the object may be less than or equal to 0.0001, the refractive indices still being substantially equal in this example. Radiation that is re-directed (e.g. scattered) by the object is then detected, for example, using a detector or other detection arrangement. The presence of a defect is detected from the re-directed radiation, for example, from an intensity distribution, or a change in an intensity distribution, of the re-directed radiation.

This embodiment is advantageous because it reduces the amount of radiation that is scattered by the object in general (i.e. not just the defect on the object). This is because the object-gas interface is replaced by an object-liquid interface in which the liquid has a refractive index which matches that of the object. In this case, little or no radiation should scatter at the interface due to the matching of the index of refraction. The only significant scattering of radiation should be due to radiation being incident on and scattered by one or more defects on the object. Detection of the defect should therefore be easier to achieve.

A dispersion curve of the liquid may intersect a dispersion curve of the object. A source of radiation providing the radiation may then be tuned until the refractive index of the object and the liquid is matched (within the bandwidth of the radiation source).

Specific embodiments will now be described, by way of example only, with reference to FIGS. 4 to 9. In FIGS. 4 to 9, the Figures have not been drawn to any particular scale. Furthermore, like features appearing in different Figures have been given the same reference numerals for consistency and clarity.

Figure 4:
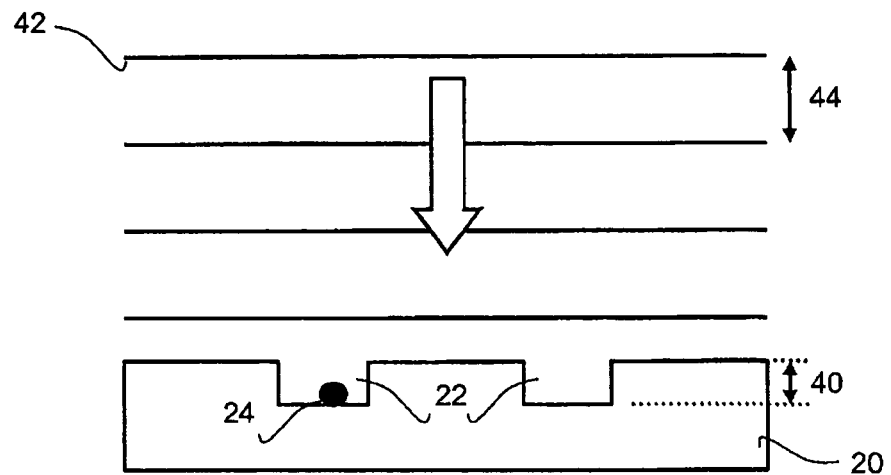
FIG. 4 schematically depicts an inspection method in accordance with an embodiment of the present invention.

FIG. 4 schematically depicts an imprint template 20. The imprint template 20 is provided with a plurality of recesses 22 which form pattern features of the imprint template 20. A defect 24 in the form of a particle is located at the bottom of one of the recesses 22. The recesses 22 have a physical depth (or an optical depth, which is equal to the physical depth of the recess multiplied by the refractive index of the medium or vacuum in the recess). The imprint template 20 may be the imprint template shown in and described with reference to any of FIGS. 1 to 3.

In the inspection method, radiation 42 is directed towards the imprint template 20. The radiation 42 has a wavelength 44 that is substantially equal to twice the optical depth 40 of the recesses 22. The radiation 42 may be directed at a specific local area or a large area (e.g. a majority or all of the area) of the imprint template 20 at any one time. Alternatively or additionally, the radiation 42 (or a source of the radiation) may be moved relative to the imprint template 20 (and/or the imprint template 20 may be moved relative to the radiation 42) to inspect a part of or the entire imprint template 20.

Figure 5:
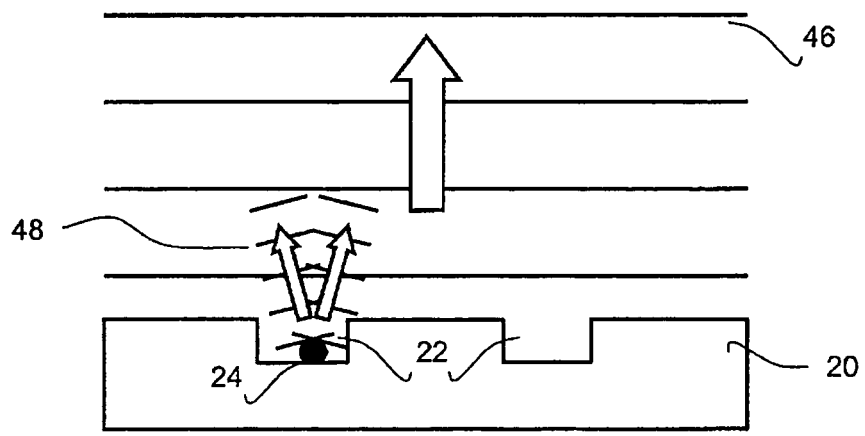
FIG. 5 schematically depicts further principles associated with the inspection method shown in and described with reference to FIG. 4.

FIG. 5 schematically depicts radiation re-directed (e.g. scattered) by the imprint template 20 and defect 24. Because the wavelength of incident radiation was twice the optical depth of the recesses 22, the scattering of radiation 46 from the recesses 22 will be reduced (in comparison with the situation in which the wavelength of radiation was not substantially equal to twice the optical depth of the recesses), since the phase difference between radiation from the bottom of the recess 22 and the top of the recess 22 will be equal to $2\pi$ (i.e. the radiation will, in practice, be in phase). In this case, the near-field of the scattered radiation 46 will ideally be continuous which will result in only a specular reflection that can be effectively suppressed with a 0-order stop.

At the same time, radiation 48 is also scattered by defect 24. Because of the continuous nature of the radiation 46 scattered by the recesses 22, the radiation 48 scattered by the defect 24 can be more easily detected and thus used to detect the presence of the defect 24. For example, the presence of the defect may be detected using dark field imaging or the like.

Figure 6:
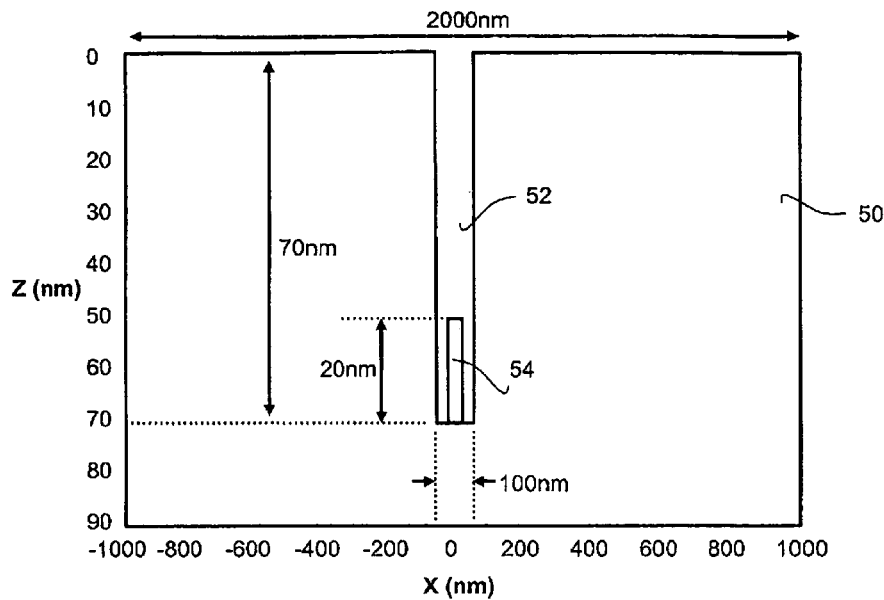
FIG. 6 schematically depicts a test structure used to test principles associated with the inspection method of an embodiment of the present invention.

FIG. 6 schematically depicts a part of a test structure 50 used in a simulation of the inspection method according to an embodiment. The test structure 50 is, in general, a grating comprising 100 nm wide recesses 52 (i.e. e.g. trenches) which each have an optical or physical depth of 70 nm. The pitch of the recesses is 2000 nm. A 20 nm long particle 54 is located at the bottom of the recess 52. In the simulation, radiation having a wavelength that is substantially equal to twice the optical depth of the recess 52 (i.e. radiation having a wavelength of 140 nm) is then directed at the test structure 50.

Figure 7:
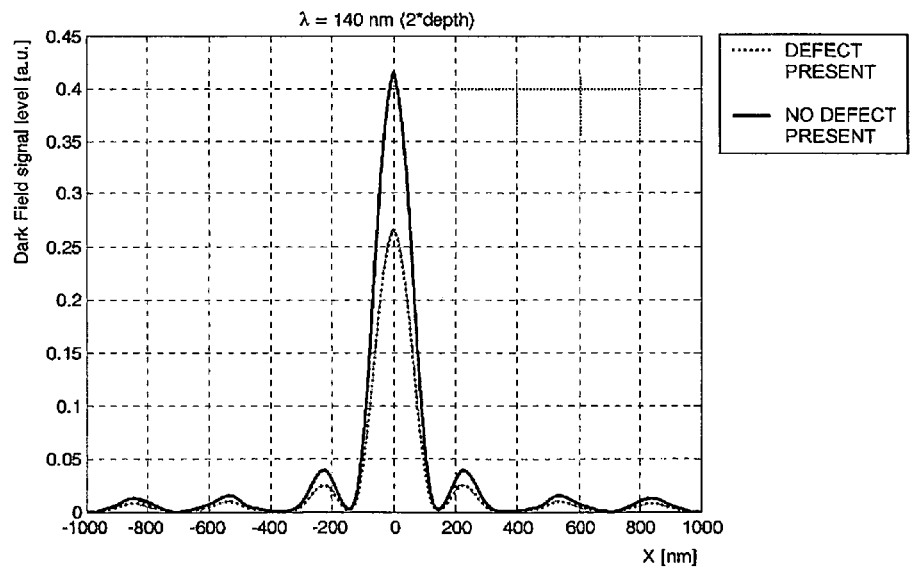
FIG. 7 is a graph schematically depicting intensity profiles of radiation scattered from the test structure shown in and described with reference to FIG. 6.

FIG. 7 is a graph that plots two signal levels. The signal levels are dark field signal levels, and represent levels of radiation scattered by the structure of FIG. 6. A first plot (indicated by a dotted-line) shows the dark field signal level when the particle (i.e. a defect) is located at the bottom of the recess. A second plot (indicated in a solid and unbroken line) shows the dark field signal level when there is no particle (i.e. no defect) at the bottom of the recess. There is a clear difference between the levels of the two signals, meaning that it is possible to be able to detect the presence (or lack of a presence) of a defect in a recess of an object.

Figure 8:
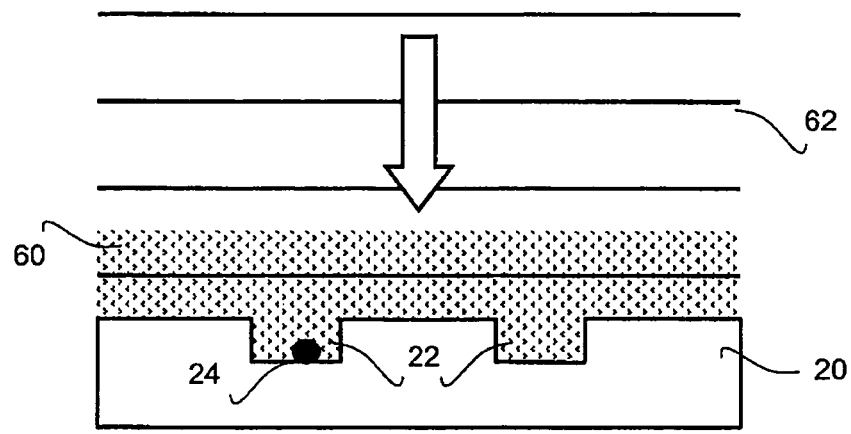
FIG. 8 schematically depicts an inspection method in accordance with a further embodiment of the present invention.

FIG. 8 schematically depicts an inspection method according to a further embodiment of the present invention, which may be used instead of, or together with, the embodiment shown in and described with reference to FIGS. 4 to 7.

In the embodiment of FIG. 8, a liquid 60 is provided that is in contact with the imprint template 20, and fills the recesses 22 of the imprint template 20. A defect 24 in the form of a particle is located at the bottom of one of the recesses 22. The imprint template 20 may be the imprint template shown in and described with reference to any of FIGS. 1 to 5.

Radiation 62 is directed through the liquid 60 and towards the imprint template 20, such that the radiation 62 is incident on the imprint template 20. The radiation 62 may be directed at a specific local area or a large area (e.g. a majority or all of the area) of the imprint template 20 at any one time. Alternatively or additionally, the radiation 62 (or a source of the radiation) may be moved relative to the imprint template 20 (and/or the imprint template 20 may be moved relative to the radiation 62) to inspect a part of or the entire imprint template 20.

As discussed above, the radiation 62 may have a wavelength which is equal to twice the optical depth of the recess 22. The wavelength 62 may have this particular wavelength in the liquid 60. In another embodiment, the radiation 62 may have another wavelength.

The liquid 60 has a refractive index which substantially matches the refractive index of the imprint template 20. For example, if the imprint template 20 is made from quartz or fused silica which has a refractive index of 1.46, the liquid 60 will have a substantially corresponding refractive index. The liquid may be, for example, $CCl_4$ which has a refractive index of 1.461. $CCl_4$ is also a cleaning agent, which may mean that inspection of the imprint template 20 may be undertaken at the same time as, before, or after cleaning of the imprint template 20.

Figure 9:
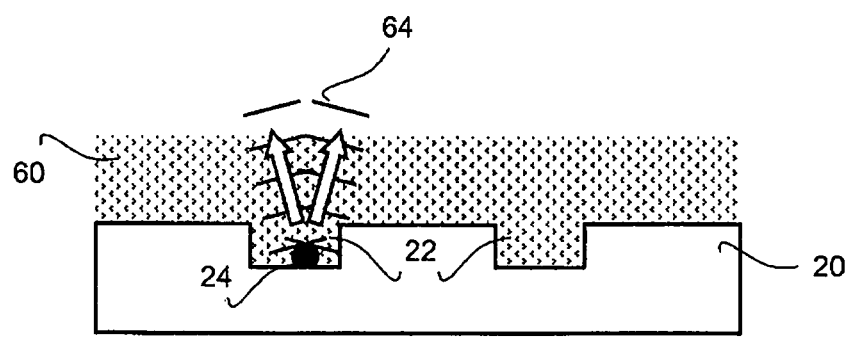
FIG. 9 schematically depicts further principles associated with the inspection method shown in and described with reference to FIG. 8.

Because the refractive index of the liquid 60 substantially matches that of the imprint template 20, there will be little or no scattering of the radiation 62 at the interface between the liquid 60 and the imprint template 20. Thus, any scattered radiation will be due to scattering of the radiation from the defect 24. FIG. 9 schematically depicts such scattering of radiation 64 from the defect 24. Since the scattering of radiation 64 should only arise from scattering by a defect 24, the presence of a defect should be easily detectable using a detector or other detection arrangement. The presence of a defect may be detected using dark field imaging, for example.

In the embodiments described above, an imprint template has been described as the object at which radiation is directed to detect the presence of a defect on that object. The inspection methods described herein may be used to inspect other objects, such as, for example, a grating or a mask suitable for use in EUV lithography. A mask suitable for use in EUV lithography may comprise, for example, one or more recesses. Such recesses may be formed, for example, in-between protruding reflective or non-reflective bodies of material which are configured to, for example, impart a pattern to an EUV radiation beam. An inspection method for inspecting an imprint template or an EUV mask may be particularly desirable, since in use a pellicle or the like may not be used to protect such a template or mask from being contaminated. In the case of an EUV mask, EUV radiation would be absorbed by such a pellicle. In the case of an imprint template, a pellicle would prevent the transfer of the pattern of the imprint template into imprintable medium.

The optical or physical depth of the recesses discussed above may be, for example, of the order of nanometers, for example, in the range of 0 nm to 100 nm, or in the range of 40 nm to 70 nm. In embodiments in which the radiation that is directed at the object has a wavelength which is twice the optical depth of the recess, this may result in the need to provide radiation having a wavelength of the order of nanometers, for example, a wavelength in the range of 0 nm to 200 nm, or in the range of 80 nm to 140 nm (for example, UV or VUV radiation). If a liquid is used to contact the object prior to radiation being directed through the liquid and at the object, the wavelength of the radiation in the liquid may be twice the optical depth of the recess. Desirably, the radiation used is substantially monochromatic (e.g. comprising only a single wavelength or a narrow range of wavelengths). This will further reduce scattering, since the embodiments discussed above are particularly suited to the use of monochromatic radiation.

Difficulties may be encountered in inspecting when the recesses in the object are arranged in a non-periodic manner. One or more embodiments of the present invention do not have such associated difficulties. Thus, embodiments of the present invention may provide an inspection method for detecting the presence of a defect on an object, wherein the object comprises one or more recesses arranged in a non-periodic manner. Recesses of an imprint template or EUV mask (or any other mask) are often provided in a non-periodic manner or arrangement.

In embodiments of the present invention described so far, radiation has been directed directly onto pattern features (e.g. recesses and/or protrusions) of the object. In an embodiment, the radiation may be directed at the pattern features and through the object. In this embodiment, the radiation may pass through the object before being re-directed (e.g. scattered or reflected) by the pattern features. This may result in an effective increase in the optical depth of the recesses, since the physical depth of the recess will be in or forming part of the object itself.

The embodiments described above have been described in relation to inspection methods. Corresponding inspection apparatus may also be provided in accordance with the embodiments of the present invention. For example, in one embodiment an inspection apparatus for detecting the presence of a defect on an object is provided. The object may comprise at least one recess having a physical depth (or an optical depth, which is equal to the physical depth of the recess multiplied by the refractive index of the medium or vacuum in the recess). The apparatus may comprise a radiation source or radiation outlet configured to direct radiation at the object. The radiation source or outlet may be configured to provide radiation having a wavelength substantially equal to twice the optical depth of the recess (which may be in air or the like, or a liquid in contact with the object). A detector is provided to detect radiation that is re-directed (e.g. scattered) by the object or the defect. A detection arrangement is also provided to detect the presence (or absence) of the defect using the re-directed radiation. For instance, a detection arrangement may be used to detect an intensity profile, or a change in an intensity profile of re-directed radiation.

According to an embodiment of the present invention, there is provided an inspection apparatus to detect the presence of a defect on an object. The object comprises at least one recess having a physical depth (or an optical depth, which is equal to the physical depth of the recess multiplied by the refractive index of the medium or vacuum in the recess). The apparatus comprises a liquid dispenser configured to provide a liquid on the object. The liquid is dispensed to be in contact with the object. A radiation source or radiation outlet may be provided to, in use, direct radiation through the liquid and at the object. The liquid that is dispensed has a refractive index which substantially matches that of the object for a wavelength of the radiation. A detector is provided to detect radiation that is re-directed (e.g. scattered) by the object or the defect. A detection arrangement is also provided to detect the presence (or absence) of the defect using the re-directed radiation. For instance, a detection arrangement may be used to detect an intensity distribution profile, or a change in an intensity distribution profile of the re-directed radiation.

In embodiments of the apparatus according to the present invention, the detector to detect the radiation that is re-directed by the object or the defect, and the detection arrangement to detect the presence (or absence) of the defect using the re-directed radiation, may be the same apparatus. The detector and/or the detection arrangement may comprise a computational device configured to detect certain intensity profiles, or to detect changes in those intensity profiles, in order to detect the presence (or absence) of a defect.

In accordance with any embodiment of the present invention, a method may be undertaken, and/or the apparatus used when the object (e.g. imprint template or EUV mask) is in-situ, for example, in an imprint lithography apparatus or an EUV lithography apparatus. The inspection may be undertaken in-between imprints or exposures. Alternatively or additionally, the inspection may be undertaken when the lithography apparatus is off-line, for example, not in operation due to a down-period or when the apparatus is not in use. In the embodiment relating to the provision of a liquid on the object for matching the refractive index, it is more likely that the method according to this embodiment will be undertaken when the object is not in use, since the presence of the liquid may prevent the object from being used as intended.

In any embodiment, once a defect has been detected, further action may be taken. For example, the object may be exchanged for a clean (defect free) object. Alternatively or additionally, the object may be cleaned. Cleaning of the object may be undertaken in a conventional manner, for example using one or more fluids or the like.

Radiation that is, or is to be, directed at the object will be generated by a radiation source. This source may be tunable, in order to be able to select a wavelength that is substantially equal to the optical depth of the recess of the object. This may be useful if the depth of recesses change across the object, or if different objects have recesses of different depths.

According to an embodiment of the invention, there is provided an object comprising at least one recess having an optical depth (which is equal to the physical depth of the recess multiplied by the refractive index of the medium or vacuum in the recess) that is substantially equal to half the wavelength of radiation that is, in use, directed at the object in order to detect the presence (or absence) of a defect on the object. The object may be an imprint template, or a mask suitable for use in EUV lithography.

While specific embodiments of the invention have been described above, it will be appreciated that the invention may be practiced otherwise than as described. For example, the invention may take the form of one or more computer programs containing one or more sequences of machine-readable instructions describing a method as disclosed above, or one or more data storage medium (e.g. semiconductor memory, magnetic or optical disk) having such one or more computer program stored therein. The one or more detectors and/or detection arrangements referred to herein may be operable when the one or more computer programs are read by one or more computer processors located within at least one component of the detector and/or detection arrangement or located in some other component that interoperates with the detector and/or the detection arrangement.

The described and illustrated embodiments are to be considered as illustrative and not restrictive in character, it being understood that only the preferred embodiments have been shown and described and that all changes and modifications that come within the scope of the inventions as defined in the claims are desired to be protected. It should be understood that while the use of words such as "preferable", "preferably", "preferred" or "more preferred" in the description suggest that a feature so described may be desirable, it may nevertheless not be necessary and embodiments lacking such a feature may be contemplated as within the scope of the invention as defined in the appended claims. In relation to the claims, it is intended that when words such as "a," "an," "at least one," or "at least one portion" are used to preface a feature there is no intention to limit the claim to only one such feature unless specifically stated to the contrary in the claim. When the language "at least a portion" and/or "a portion" is used the item can include a portion and/or the entire item unless specifically stated to the contrary.

The invention claimed is:

1. An inspection method for detecting the presence or absence of a defect on an object, the object comprising a recess having a physical depth, the method comprising:
    directing radiation at the object, the radiation having a wavelength that is substantially equal to twice an optical depth of the recess;
    detecting radiation that is re-directed by the object or a defect on the object; and
    determining the presence or absence of a defect in the recess from the re-directed radiation, the defect having a size smaller than the optical depth.

2. The inspection method of claim 1, wherein the optical or physical depth of the recess is in the range of 1 nm to 100 nm.

3. The inspection method of claim 1, wherein the radiation has a wavelength in the range of 1 nm to 200 nm.

4. The inspection method of claim 1, wherein the radiation is substantially monochromatic.

5. The inspection method of claim 1, wherein the re-directed radiation comprises scattered radiation.

6. The inspection method of claim 1, wherein the presence or absence of the defect is determined from an intensity distribution, or a change in an intensity distribution, of the re-directed radiation.

7. The inspection method of claim 1, wherein the presence or absence of the defect is detected using dark field imaging.

8. The inspection method of claim 1, wherein the object comprises a plurality of recesses.

9. The inspection method of claim 8, wherein the plurality of recesses are arranged in a non-periodic manner.

10. The inspection method of claim 1, wherein the object comprises fused silica or quartz.

11. The inspection method of claim 1, wherein the object is an imprint template, or a mask suitable for use in EUV lithography.

12. An inspection method for detecting the presence or absence of a defect on an object, the object comprising a recess having a physical depth, the method comprising:
    providing a liquid that is in contact with a side of the object and into the recess;
    directing radiation through the liquid and at the object, the liquid having a refractive index which substantially matches that of a wall of the recess for a wavelength of the radiation;
    detecting radiation re-directed by the object or a defect on the object; and
    determining the presence or absence of a defect on the side of the object, the defect being other than the recess, from the re-directed radiation.

13. The inspection method of claim 12, wherein the radiation has a wavelength in the liquid that is substantially equal to twice an optical depth of the recess.

14. The inspection method of claim 12, wherein the presence or absence of the defect is determined from an intensity distribution, or a change in an intensity distribution, of the re-directed radiation.

15. The inspection method of claim 12, wherein the presence or absence of the defect is detected using dark field imaging.

16. An inspection apparatus to detect the presence or absence of a defect on an object, the object comprising a recess having a physical depth, the apparatus comprising:
    a radiation outlet configured to direct radiation at the object, the radiation outlet configured to direct radiation having a wavelength that is substantially equal to twice an optical depth of the recess;
    a detector configured to detect the radiation that is re-directed by the object or a defect on the object; and
    a detection arrangement configured to determine the presence or absence of a defect in the recess using the re-directed radiation, the defect having a size smaller than the optical depth.

17. The apparatus of claim 16, further comprises a radiation source to supply the radiation to the radiation outlet.

18. An inspection apparatus to detect the presence or absence of a defect on an object, the object comprising a recess having a physical depth, the apparatus comprising:
    a liquid dispenser configured to provide a liquid on, and in contact with, a side of the object and into the recess;
    a radiation outlet configured to, in use, direct radiation through the liquid and at the object, the liquid having a refractive index which substantially matches that of a wall of the recess for a wavelength of the radiation;
    a detector configured to detect the radiation that is re-directed by the object or a defect on the object; and
    a detection arrangement configured to determine the presence or absence of a defect on the side of the object, the defect being other than the recess, using the re-directed radiation.

19. An inspection method for detecting the presence or absence of a defect on an object, the object comprising a recess having an optical depth and the recess not being a defect, the method comprising:
    directing radiation at the object including at the recess, the radiation having a wavelength that is substantially equal to twice the optical depth of the recess;
    detecting at least part of the radiation that is re-directed by the object or a defect on the object; and
    determining the presence or absence of a defect having a size smaller than the optical depth from the re-directed radiation.

* * * * *

UNITED STATES PATENT AND TRADEMARK OFFICE
CERTIFICATE OF CORRECTION

PATENT NO.         : 8,830,455 B2
APPLICATION NO.    : 12/805808
DATED              : September 9, 2014
INVENTOR(S)        : Arie Jeffrey Den Boef et al.

It is certified that error appears in the above-identified patent and that said Letters Patent is hereby corrected as shown below:

On Title Page, Item (75) Inventors, Line 2
  replace "Eendracht"
  with --Deurne--.

Signed and Sealed this
Thirtieth Day of December, 2014

Michelle K. Lee
*Deputy Director of the United States Patent and Trademark Office*